(12) United States Patent
Saito

(10) Patent No.: US 6,611,719 B2
(45) Date of Patent: *Aug. 26, 2003

(54) CANCER THERMOTHERAPY

(75) Inventor: Yoshiaki Saito, Nigata Pref. (JP)

(73) Assignee: Niigta University, Niigta Pref. (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 40 days.

(21) Appl. No.: 09/770,845

(22) Filed: Jan. 26, 2001

(65) Prior Publication Data

US 2002/0010501 A1 Jan. 24, 2002

(30) Foreign Application Priority Data

Jul. 4, 2000 (JP) ........................... 2000-201856

(51) Int. Cl.[7] .................................................. A61F 2/00
(52) U.S. Cl. ........................... 607/101; 607/99; 606/27; 606/33; 330/43; 330/45; 330/56; 128/898
(58) Field of Search .............................. 607/96–102, 90, 607/91; 606/27–33; 330/43–46, 52–57; 128/898

(56) References Cited

U.S. PATENT DOCUMENTS

| | | | |
|---|---|---|---|
| 4,316,453 A | | 2/1982 | Harrison |
| 4,586,516 A | | 5/1986 | Turner |
| 4,660,572 A | * | 4/1987 | Maruyama et al. .......... 128/804 |
| 4,951,688 A | * | 8/1990 | Keren .......................... 128/804 |
| 5,010,897 A | * | 4/1991 | Leveen ......................... 128/804 |
| 5,163,446 A | * | 11/1992 | Saitoh .......................... 128/804 |
| 5,492,122 A | * | 2/1996 | Button et al. ............ 128/653.2 |
| 5,690,109 A | * | 11/1997 | Govind et al. ........... 128/653.2 |

FOREIGN PATENT DOCUMENTS

| | | |
|---|---|---|
| DE | 197 26 570 C1 | 12/1998 |
| DE | 197 27 967 A1 | 1/1999 |
| EP | 0 595 104 A1 | 5/1994 |
| GB | 2 047 099 A | 11/1980 |
| RU | SU 1777914 A1 | 11/1992 |
| WO | WO 89/07469 | 8/1989 |

* cited by examiner

*Primary Examiner*—Linda C. M. Dvorak
*Assistant Examiner*—Ahmed Farah
(74) *Attorney, Agent, or Firm*—Knobbe Martens Olson & Bear LLP

(57) ABSTRACT

A given high frequency electric power introduced into a cavity resonator is resonated in the long direction of the cavity resonator on an excited mode with a constant electric field intensity along the long direction of the cavity resonator. Then, a human body is set on a table 2 in the cavity resonator so that its body axis can match the long direction of the cavity resonator. Then, the resonated high frequency electric power is applied to the human body.

13 Claims, 4 Drawing Sheets

CANCER THERMOTHERAPY

BACKGROUND OF THE INVENTION

1) Field of the Invention

This invention relates to a cancer thermotherapy, particularly to a cancer thermotherapy to set a human body in a cavity resonator and heat a given part of the human body.

2) Description of the Prior Art

Conventionally, a variety of cancer therapies have been proposed, but these conventional cancer therapies can not heat a deep part of a human body effectively.

One of the causes is that in the conventional therapies, excited modes to maximize their electric field distribution before putting the human body in at a center of a body axis are employed. Herein, the "body axis" means a line between the head and legs of the human body. That is, if the human body is put in a cavity resonator with such an excited mode, its predetermined preferable electric field distribution changes, so that a desired deep part of the human body can not be heated sufficiently due to its weak electric field intensity at the deep part thereof.

The other cause is that, although in the conventional therapies, a high frequency electric power equal to the resonance frequency of the cavity resonator must be applied, the resonance frequency of the cavity resonator becomes indefinite due to the large loss of the cavity resonator as the human body is put in.

SUMMARY OF THE INVENTION

It is an object of the present invention to provide a cancer thermotherapy capable of heating a desired deep part of the human body effectively and thereby, performing the cancer thermotherapy for the human body effectively.

For achieving the above object, this invention relates to a cancer thermotherapy comprising the steps of:

resonating a given high frequency electric power introduced into a cavity resonator in the long direction of the cavity resonator on an excited mode with a constant electric field intensity, setting a human body in the cavity resonator so that the body axis of the human body can match the long direction of the cavity resonator, and applying the resonated high frequency electric power in the excited mode to the human body, whereby a given part of the human body is heated and the cancer spawn at the given part is treated.

The cancer thermotherapy of the present invention resonates, in the cavity resonator, the high frequency electric power introduced into the cavity resonator on the excited mode with a constant electric field intensity in its long direction, which is different from the above conventional therapies. Then, a human body is put in the cavity resonator in the above condition so that the body axis of the human body can match the long direction of the cavity resonator.

In this case, the above high frequency electric power with the constant electric field intensity is applied to the human body in the above resonant condition. However, when the high frequency electric power is introduced into the human body, it is reflected at one forefront of the human body due to the difference in electric constant between the human body and the interior space of the cavity resonator. The reflected high frequency electric power is reflected again at the other forefront of the human body, and thus, the high frequency electric power is concentrated on a desired part of the human body.

The reflected high frequency electric power is superposed at the desired part of the human body with time, and thus, the electric field intensity is increased at the desired part. As result, a deep part of the human body can be heated effectively, and the cancer spawned at the deep part can be treated effectively.

Although the above conventional cancer thermotherapy can have only about 10% complete recovery rate, the cancer thermotherapy of the present invention can develop the complete recovery rate up to about 50%.

BRIEF DESCRIPTION OF THE DRAWINGS

For better understanding of the present invention, reference is made to the attached drawings, wherein.

DESCRIPTION OF THE PREFERRED EMBODIMENTS

This invention will be described in detail with reference to figures.

Figure 1:
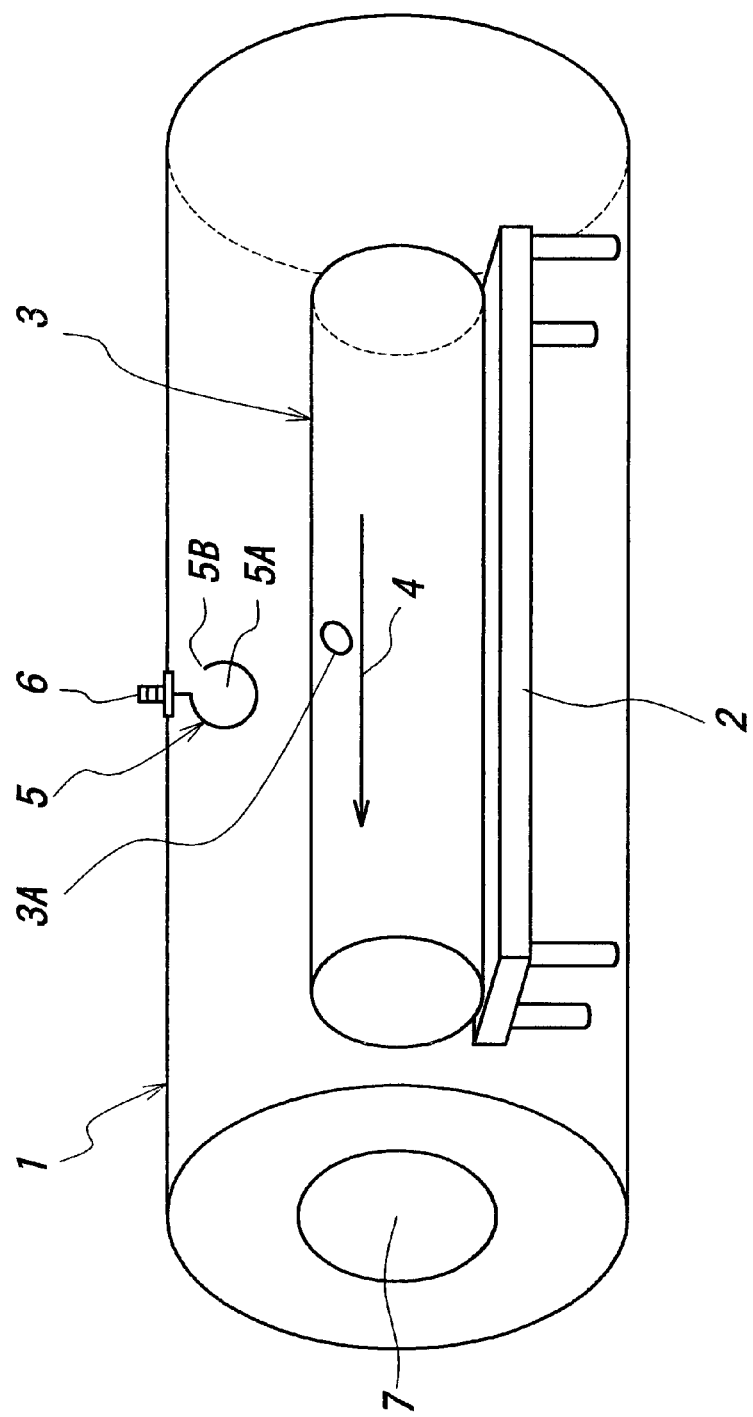
FIG. 1 is a perspective view showing a cancer thermotherapy apparatus preferably employed in the cancer thermotherapy of the present invention.

FIG. 1 is a perspective view showing a cancer thermotherapy apparatus preferably employed in the cancer thermotherapy of the present invention.

The cancer thermotherapy apparatus depicted in FIG. 1 has a cylindrical cavity resonator 1 and a table 2 to set a human body 3 thereon in the resonator. Herein, the human body 3 is depicted as a column for simplification. A loop antenna 5 is provided on the upper wall of the cavity resonator 1 via a connector 6 so that its loop face 5A can be parallel to the long direction of the cavity resonator 1.

The connector 6 is connected to an external high frequency electric power supply (not shown) via an impedance matching device (not shown), and thereby, a high frequency electric power is introduced into the cavity resonator 1 from the external high frequency electric power supply. The forefront 5B of the loop antenna 5 is opened so as to excite and resonate the introduced high frequency electric power in the cavity resonator 1. Moreover, an opening 7 to put the human body 3 in or out of the cavity resonator 1 is formed at the left end of the resonator. When the human body 3 is treated, the opening 7 is closed by a given lid.

In the cancer thermotherapy of the present invention, a given high frequency electric power is introduced into the cavity resonator 1 from the external high frequency electric power supply through the connector 6 before the human body 3 is set in the cavity resonator 1. Then, the introduced high frequency electric power is excited by the loop antenna 5 and resonated at a given frequency in the cavity resonator 1. In this case, since the loop antenna 5 has the loop face 5A parallel to the long direction of the cavity resonator 1, the high frequency electric power is resonated on an excited mode with its constant electric field intensity along the long direction of the cavity resonator 1, that is, on an electric field intensity-unchangeable excited mode.

Then, the human body 3 is put in the cavity resonator 1 in the above resonant condition from the opening 7, and is set on the table 2 so that its body axis 4 can match the long direction of the cavity resonator 1. In this case, a new resonated frequency electric power in the above excited mode with the constant electric field intensity is applied to the human body 3. Because of the difference in electric constant between the human body 1 and the interior of the cavity resonator 1, the high frequency electric power in the above excited mode is reflected at one forefront of the human body 3.

The reflected high frequency electric power is reflected at the other forefront of the human body 3 again, and is concentrated on, for example, a given part 3A of the human body 3. The reflected high frequency electric powers are superposed at the given part with time and thus, the electric field intensity is increased at the given part. As a result, the given part 3A can be deeply heated effectively and the cancer spawned in the given part can be treated effectively.

In the cancer thermotherapy of the present invention using the apparatus shown in FIG. 1, however, the near part of the human body 3 to the loop antenna 5 may be heated effectively and the farther part of the human body may not be heated effectively because the heating effectiveness is decreased at the farther part of the human body, so that the farther part may not be heated to a predetermined temperature.

In this case, it is preferable that an additional loop antenna is provided on the lower wall of the cavity resonator 1 so as to sandwich the human body 3 with the loop antenna 5. Then, respective high frequencies are applied to the loop antenna 5 and the additional antenna in antiphase. As a result, the heating effectivenesses from the two loop antennas are added up and thus, the human body can be heated effectively in its cross section.

In this case, the center of the human body in the cross section has a tendency to be heated at the most. Therefore, the center of the human body corresponding to the deepest part thereof can be heated effectively and thus, the cancer spawned at the center can be treated effectively.

If the additional antenna is provided so that its loop direction can be opposite to that of the loop antenna 5, respective high frequency electric powers are applied to the additional antenna and the loop antenna 5 in phase in order to perform the above heating effectiveness.

Moreover, if three or more loop antennas are provided in the cavity resonator and the intensities and phases of high frequency electric powers to be applied to the loop antennas are controlled appropriately, any parts of the human body can be heated effectively.

Although the loop antenna can have any length, it is preferable that it has a quarter length of the wavelength of the high frequency electric power to be introduced into the cavity resonator. As a result, the high frequency electric power can be excited effectively and resonated.

Moreover, although the loop face 5A of the loop antenna 5 depicted in FIG. 1 has a substantially circular shape, it has preferably a laterally long elliptical shape or a rectangular shape.

Figure 2:
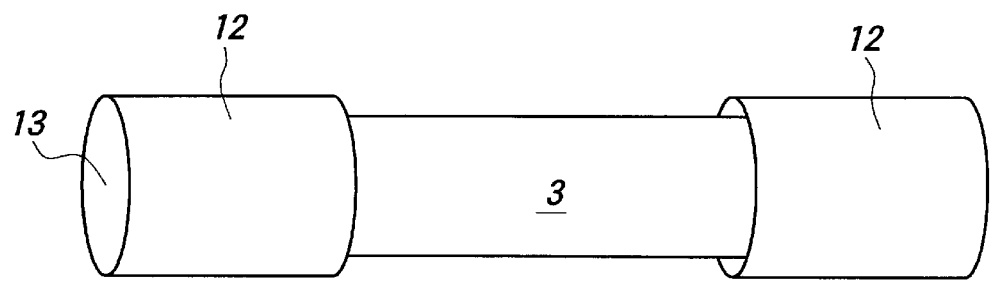
FIG. 2 is an explanatory view for a preferred embodiment in the cancer thermotherapy of the present invention.

FIG. 2 is an explanatory view for a preferred embodiment in the cancer thermotherapy of the present invention.

In the above cancer thermotherapy of the present invention, parts of the human body not to be heated such as a head and a foot may be heated. In this case, it is preferable to cover the parts not to be heated with tubular metallic members 12 as shown in FIG. 2. Since the above resonated high frequency electric power is not introduced inside the metallic members, the parts covered with the metallic members can not be heated.

Moreover, the bottom surface of one of the metallic members 12 is preferably covered with a metallic plate 13 as shown in FIG. 2. In this case, the high frequency electric power can not be introduced more effectively inside the metallic members 12.

The metallic members 12 does not always have the above tubular shape shown in FIG. 2, and can have any shapes in accordance with the human body shapes.

Figure 3:
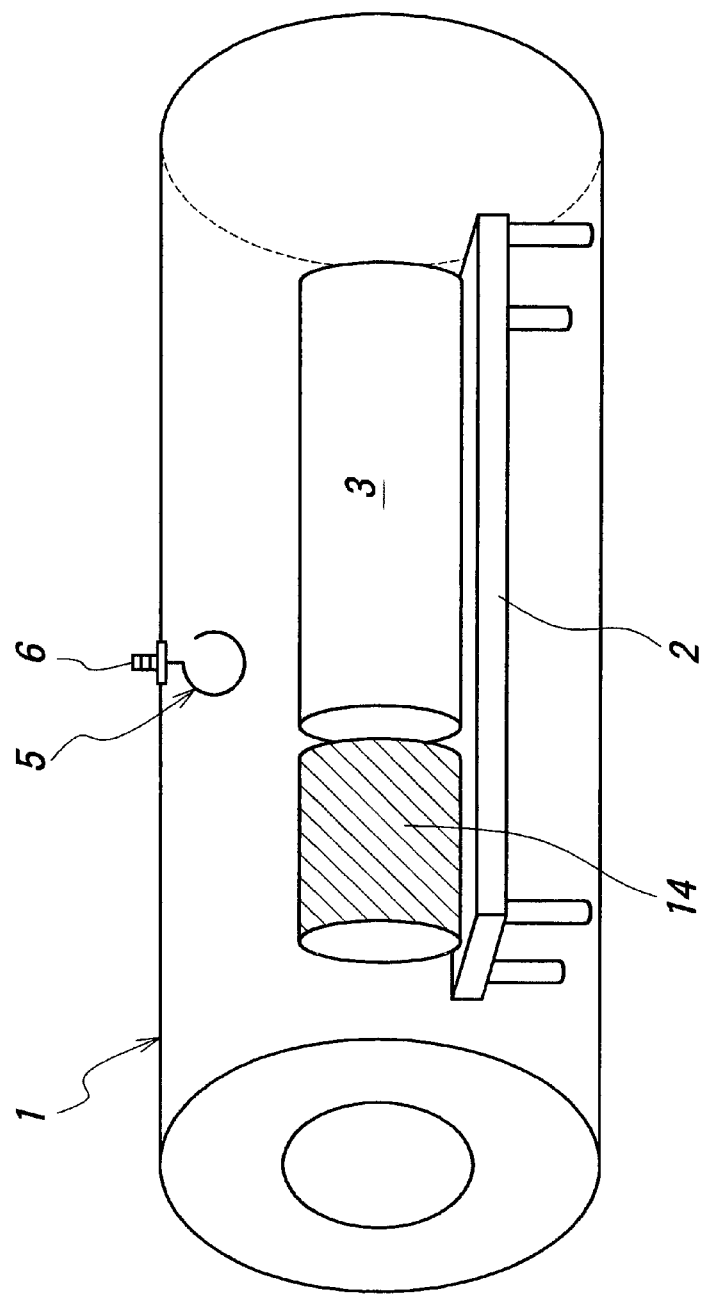
FIG. 3 is an explanatory view for another preferred embodiment in the cancer thermotherapy of the present invention.

FIG. 3 is an explanatory view for another preferred embodiment in the cancer thermotherapy of the present invention. Similar parts to the ones in FIG. 1 are designated by the same reference numerals.

The resonant frequency of the cavity resonator 1 changes in accordance with the size and shape of the human body. However, in view of the frequency dependence in the external high frequency electric power supply, cable length or the impedance matching device, it is desired that the cavity resonator 1 has a constant resonant frequency. Therefore, a resonant frequency controlling member 14 is set at a predetermined position in the cavity resonator 1 as shown in FIG. 3 to make constant the resonant frequency thereof.

Concretely, the above constant process is performed by adjusting the size, length, material and position of the resonant frequency controlling member 14. The resonant frequency controlling member 14 may be positioned not only on the table 2 to set the human body on, but also on a pedestal located at a given position in the cavity resonator 1.

The resonant frequency controlling member 14 may be made of a metallic material such as Cu, Al, Fe, a ceramic material, a dielectric material such as Ti and oil, and a human body-equivalent phantom such as TX151, interfacial agent liquid and water. Then, by making the resonant frequency controlling member 14 of the above appropriate material, the resonant frequency of the cavity resonator can be controlled.

In the case of using the tubular metallic member as shown in FIG. 2, the resonant frequency of the cavity resonator can be made constant by adjusting the diameter, the length and the position in the resonator of the metallic member.

Figure 4:
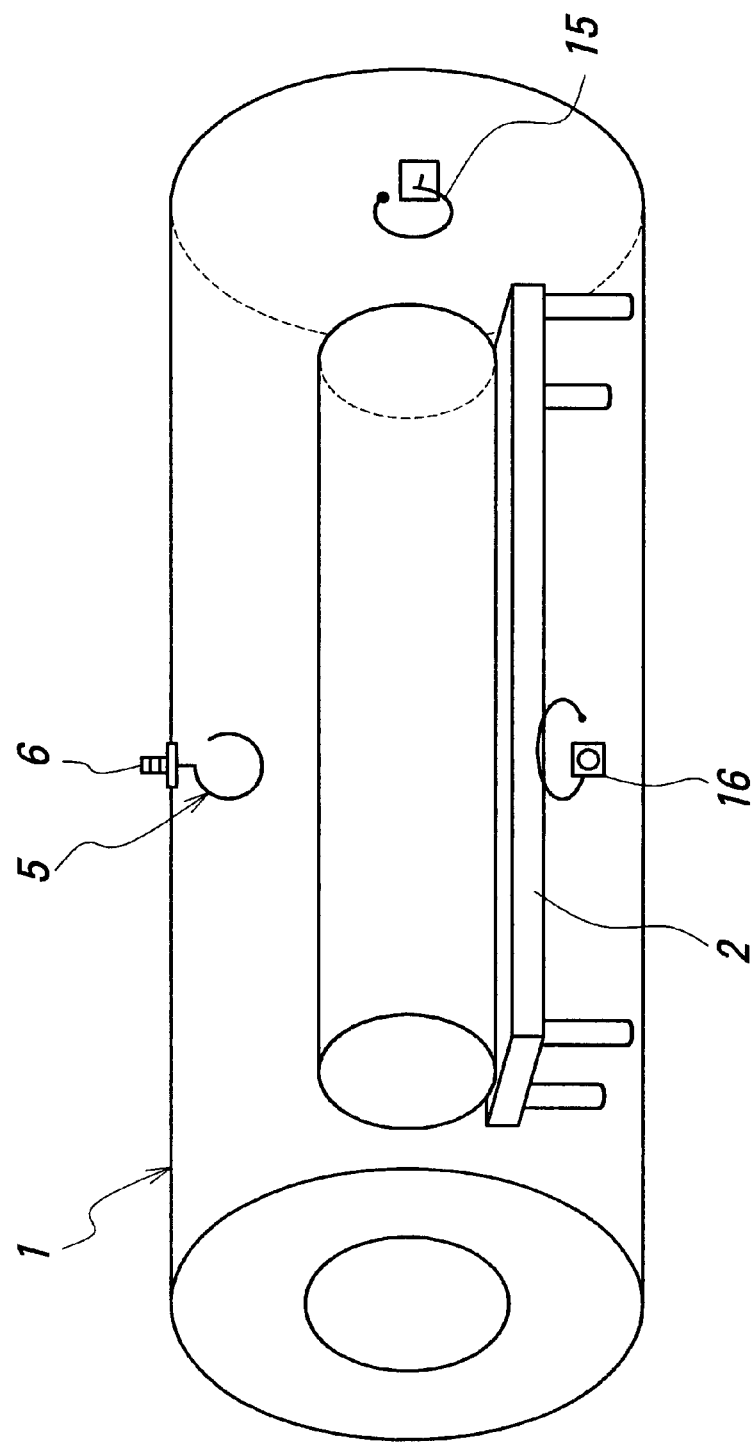
FIG. 4 is an explanatory view for a measuring method of a resonance frequency in the cancer thermotherapy of the present invention.

Next, a measuring method of a resonant frequency in the cancer thermotherapy of the present invention will be described. FIG. 4 is an explanatory view for the measuring method.

As a predetermined part of the human body is heated effectively according to the cancer thermotherapy of the present invention, the resonated high frequency electric power is absorbed into the human body largely, resulting in the large degradation of the Q value of the cavity resonator. As a result, the resonant frequency of the cavity resonator can not be measured from its frequency-resonant characteristic.

In this case, as shown in FIG. 4, an exciting antenna 15 is provided on the right end of the cavity resonator 1 in addition to the loop antenna 5 so that its loop face can be orthogonal to that of the loop antenna 5 and a receiving antenna 16 is provided on the lower wall of the cavity resonator 1. Then, a high frequency electric power is supplied into the cavity resonator 1 from a variable high frequency electric power generator through the exciting antenna 15. In this case, the supplied high frequency electric power is resonated in the cavity resonator 1 without its absorption into the human body 3. Therefore, the high frequency electric power is received at the receiving antenna 16, and thus, the resonant frequency of the cavity resonator 1 can be measured from the frequency of the maximum received signal thereat.

In FIG. 4, the exciting antenna is provided on the right end of the cavity resonator 1 so that its loop face can be orthogonal to that of the loop antenna and the receiving antenna is provided on the lower wall of the cavity resonator. However, the receiving antenna may be provided on the right end and the exciting antenna may be provided on the lower wall so that its loop face can be orthogonal to that of the loop antenna only if the supplied high frequency electric power is resonated in the cavity resonator through its resonant condition. Moreover, the exciting antenna and the receiving antenna may be provided on the left end and the right end of the cavity resonator, respectively, so that their loop faces can be orthogonal to that of the loop antenna.

Although the present invention was described in detail with reference to the above example, this invention is not limited to the above disclosure and every kind of variation and modification may be made without departing from the scope of the present invention.

For example, although the cylindrical cavity resonator is employed in the above embodiment, an elliptical cavity resonator, a square pole cavity resonator or a polygonal cavity resonator may be used.

According to the cancer thermotherapy of the present invention, a given part of a human body can be deeply heated effectively and thus, the cancer thermotherapy can be performed for the human body effectively.

What is claimed is:

1. A cancer thermotherapy comprising the steps of:
    resonating a given high frequency electric power introduced into a cavity resonator in the long direction of the cavity resonator on an excited mode with a constant electric field intensity, wherein the high frequency electric power is resonated using a loop antenna having a loop face disposed in parallel to the long direction of the cavity resonator,
    setting a human body in the cavity resonator to match the longitudinal body axis of the human body and the long direction of the cavity resonator, and
    applying the resonated high frequency electric power in the excited mode to the human body, whereby a given part of the human body is heated and the cancer spawn at the given part is treated.

2. A cancer thermotherapy as defined in claim 1, wherein the human body is heated so that the center of the human body in the cross section can have a maximum temperature by a respective high frequency electric powers in antiphase applied to two loop antennas with the same loop direction provided so that they can sandwich the human body and their loop faces can be parallel to the long direction of the cavity resonator.

3. A cancer thermotherapy as defined in claim 1, wherein the human body is heated so that the center of the human body in the cross section can have a maximum temperature by a respective high frequency electric powers in phase applied to two loop antennas with their respective opposite loop directions provided so that they can sandwich the human body and their loop faces can be parallel to the long direction of the cavity resonator.

4. A cancer thermotherapy as defined in claim 1, wherein any part of the human body is heated by controlling the electric power intensities and phases of a respective high frequency electric powers applied to plural loop antennas provided so that they can surround the human body and their loop faces can be parallel to the long direction of the cavity resonator.

5. A cancer thermotherapy as defined in any one of claims 2–4, wherein the loop antenna has a quarter length of the wavelength of the high frequency electric power.

6. A cancer thermotherapy as defined in any one of claims 2–4, wherein the loop antenna has a laterally long elliptical loop face or a rectangular loop face.

7. A cancer thermotherapy as defined in any one of claims 1–4, wherein a predetermined part of the human body is covered with a cylindrical metallic member, and thereby, a given part of the human body except the covered predetermined part thereof is heated.

8. A cancer thermotherapy as defined in claim 7, wherein one bottom surface of the cylindrical metallic member is covered with a metallic plate.

9. A cancer thermotherapy as defined in claim 7, wherein the resonant frequency of the cavity resonator is adjusted by controlling the diameter, the length, and the position in the cavity resonator of the cylindrical metallic member.

10. A cancer thermotherapy as defined in any one of claims 1–4, wherein the resonant frequency of the cavity resonator is adjusted by a resonant frequency controlling member provided at a predetermined position in the cavity resonator.

11. A cancer thermotherapy as defined in claim 10, wherein the resonant frequency controlling member is made of a metallic material, a ceramic material or a human body-equivalent phantom.

12. A cancer thermotherapy as defined in any one of claims 1–4, wherein the resonant frequency of the cavity resonator is measured by a pair of exciting antenna and receiving antenna.

13. A cancer thermotherapy as defined in claim 12, wherein at least one of the exciting antenna and the receiving antenna is provided so that its loop face can be orthogonal to that of the loop antenna.

* * * * *